(12) United States Patent
Kubo (10) Patent No.: US 8,224,198 B2
(45) Date of Patent: Jul. 17, 2012

(54) HUMIDITY DETECTING DEVICE AND IMAGE FORMING APPARATUS INCLUDING THE SAME

(75) Inventor: Isao Kubo, Nagoya (JP)

(73) Assignee: Brother Kogyo Kabushiki Kaisha, Nagoya-shi, Aichi-ken (JP)

( * ) Notice: Subject to any disclaimer, the term of this patent is extended or adjusted under 35 U.S.C. 154(b) by 545 days.

(21) Appl. No.: 12/411,986

(22) Filed: Mar. 26, 2009

(65) Prior Publication Data

US 2009/0297184 A1 Dec. 3, 2009

(30) Foreign Application Priority Data

Jun. 2, 2008 (JP) ................................ 2008-144769

(51) Int. Cl.
 G03G 15/00 (2006.01)
 G03G 21/00 (2006.01)
 G03G 21/20 (2006.01)
(52) U.S. Cl. .......................................... 399/44; 399/94
(58) Field of Classification Search .................... 399/44, 399/94, 97
 See application file for complete search history.

(56) References Cited

U.S. PATENT DOCUMENTS

| 5,077,566 | A | * | 12/1991 | Ochiai et al. ..................... 347/55 |
| 5,148,218 | A | * | 9/1992 | Nakane et al. ..................... 399/9 |
| 5,170,210 | A | * | 12/1992 | Saruwatari ....................... 399/44 |
| 5,656,928 | A | * | 8/1997 | Suzuki et al. ................. 324/71.1 |
| 6,281,963 | B1 | * | 8/2001 | Takahata et al. ................ 355/41 |
| 7,597,001 | B2 | * | 10/2009 | Hayakawa ................. 73/335.05 |
| 7,680,422 | B2 | * | 3/2010 | Nakaue et al. ................... 399/44 |
| 7,899,346 | B2 | * | 3/2011 | Kubo et al. ...................... 399/44 |

FOREIGN PATENT DOCUMENTS

| JP | 01088144 A | * | 4/1989 |
| JP | 07311169 A | * | 11/1995 |
| JP | 2001-147139 | | 5/2001 |
| JP | 2005221484 | | 8/2005 |
| JP | 2006-275761 | | 10/2006 |
| JP | 2007232428 A | * | 9/2007 |
| JP | 2007248455 A | * | 9/2007 |
| JP | 2007263702 A | * | 10/2007 |

* cited by examiner

Primary Examiner — David Gray
Assistant Examiner — Fred L Braun
(74) Attorney, Agent, or Firm — Banner & Witcoff, Ltd.

(57) ABSTRACT

A humidity detecting device includes a humidity sensor, which detects humidity using a change in an impedance by humidity, and which generates a humidity detection signal according to application of an AC voltage, a detecting unit that detects the impedance of the humidity sensor based on the humidity detection signal, a switching unit that switches a frequency of the AC voltage to at least a first frequency and a second frequency, the humidity sensor being a first impedance at the first frequency and a second impedance at the second frequency, a temperature sensor that detects ambient temperature of the humidity sensor, a calculating unit that calculates a difference and/or a change rate between the first impedance and the second impedance, a discriminating unit that discriminates the humidity sensor based on the difference and/or the change rate, and a control unit that performs processing corresponding to the discriminated humidity sensor.

14 Claims, 10 Drawing Sheets

| A/D (8 BITS) | VOLTAGE [V] | TEMPERATURE | | | | | | | | | | |
|---|---|---|---|---|---|---|---|---|---|---|---|---|
| | | 5°C | 6°C | 7°C | 8°C | 9°C | 10°C | 11°C | 12°C | 13°C | 14°C | 15°C |
| 0 | 0 | | | | | | | | | | | |
| 1 | 0.020 | 25 | 25 | 24 | 24 | 23 | 23 | 22 | 22 | 21 | 21 | 20 |
| 2 | 0.039 | 28 | 27 | 27 | 26 | 26 | 25 | 25 | 25 | 24 | 24 | 23 |
| 3 | 0.059 | 39 | 29 | 28 | 28 | 28 | 27 | 27 | 26 | 26 | 25 | 25 |
| 4 | 0.078 | 31 | 30 | 30 | 29 | 29 | 28 | 28 | 28 | 27 | 27 | 26 |
| 5 | 0.098 | 32 | 31 | 31 | 30 | 30 | 30 | 29 | 29 | 28 | 28 | 27 |
| 6 | 0.117 | 33 | 32 | 32 | 31 | 31 | 31 | 30 | 29 | 29 | 29 | 28 |
| 7 | 0.137 | 34 | 33 | 33 | 32 | 32 | 32 | 31 | 30 | 30 | 29 | 29 |
| 8 | 0.156 | 34 | 34 | 33 | 33 | 33 | 32 | 32 | 31 | 31 | 30 | 29 |
| 9 | 0.176 | 35 | 34 | 34 | 34 | 33 | 33 | 32 | 32 | 31 | 31 | 30 |
| 10 | 0.195 | 36 | 35 | 35 | 35 | 34 | 34 | 33 | 32 | 32 | 31 | 31 |
| 11 | 0.215 | 36 | 36 | 35 | 35 | 34 | 34 | 33 | 33 | 32 | 32 | 31 |
| 12 | 0.234 | 37 | 36 | 36 | 36 | 35 | 35 | 34 | 33 | 33 | 32 | 32 |
| 13 | 0.254 | 37 | 37 | 36 | 36 | 35 | 35 | 34 | 34 | 33 | 32 | 32 |
| 14 | 0.273 | 38 | 37 | 37 | 36 | 36 | 36 | 35 | 34 | 33 | 33 | 33 |
| 15 | 0.293 | 38 | 38 | 37 | 37 | 36 | 36 | 35 | 35 | 34 | 33 | 33 |
| 16 | 0.313 | 39 | 38 | 38 | 37 | 37 | 36 | 36 | 35 | 34 | 34 | 34 |
| 17 | 0.332 | 39 | 39 | 38 | 38 | 37 | 37 | 36 | 36 | 35 | 34 | 34 |
| 18 | 0.352 | 39 | 39 | 38 | 38 | 38 | 37 | 36 | 36 | 35 | 34 | 34 |
| 19 | 0.371 | 40 | 39 | 39 | 38 | 38 | 37 | 37 | 36 | 36 | 35 | 35 |
| 20 | 0.391 | 40 | 40 | 39 | 39 | 38 | 38 | 37 | 37 | 36 | 36 | 35 |

HUMIDITY SENSOR DETECTED VALUE

HUMIDITY DETECTING DEVICE AND IMAGE FORMING APPARATUS INCLUDING THE SAME

CROSS-REFERENCE TO RELATED APPLICATIONS

This application claims priority from Japanese Patent Application No. 2008-144769 filed on Jun. 2, 2008, the entire subject matter of which is incorporated herein by reference.

TECHNICAL FIELD

Aspects of the invention relate to a humidity detecting device and an image forming apparatus including the humidity detecting device, and specifically to appropriateness of a humidity sensor used in the humidity detecting device.

BACKGROUND

There has been proposed a technique for reading an appropriate measured value from a detected value from a humidity sensor varying depending on a change in temperature based on a data table created by changing a set value of temperature by a physical quantity change device (see, for example, JP-A-2006-27576).

SUMMARY

Illustrative aspects of the invention provide a humidity detecting device capable of easily discriminating a kind of a humidity sensor and performing appropriate processing according to the kind of the humidity sensor.

DETAILED DESCRIPTION

<General Overview>

Generally, in a resistance variable type humidity sensor for detecting humidity using a change in an impedance (resistance) by humidity, an impedance of the resistance variable type humidity sensor changes according to ambient temperature. Further, change characteristics of an impedance by humidity vary greatly depending on a kind of the humidity sensor, so that it is desirable to properly use the humidity sensors according to a use environment in order to perform appropriate control of the humidity sensor. In that case, it may be considered to use impedance characteristics varying depending on a kind of the sensor in order to discriminate a kind of the used humidity sensor.

However, it is almost impossible to measure impedance characteristics with respect to humidity and temperature of a used humidity sensor in a use field. Further, it takes time and labor to discriminate a kind of the humidity sensor by measuring the impedance characteristics of the used humidity sensor in a laboratory and is complicated.

Therefore, illustrative aspects of the invention is to provide a humidity detecting device capable of easily discriminating a kind of a humidity sensor and performing appropriate processing according to the kind of the humidity sensor.

According to a first aspect of the invention, there is provided a humidity detecting device comprising: a humidity sensor, which detects humidity using a change in an impedance by humidity, and which generates a humidity detection signal according to application of an AC voltage; an applying unit that applies the AC voltage to the humidity sensor; a detecting unit that detects the impedance of the humidity sensor based on the humidity detection signal; a switching unit that switches a frequency of the AC voltage to at least a first frequency and a second frequency that is different from the first frequency, the impedance of the humidity sensor being a first impedance at the first frequency, the impedance of the humidity sensor being a second impedance at the second frequency; a temperature sensor that detects ambient temperature of the humidity sensor; a calculating unit that uses detected values of the first impedance and the second impedance detected by the detecting unit so as to calculate at least one of a difference and a change rate between the first impedance and the second impedance; a discriminating unit that discriminates the humidity sensor based on the at least one of the difference and the change rate between the first impedance and the second impedance; and a control unit that performs processing corresponding to the discriminated humidity sensor when the humidity detecting device detects the humidity.

According to a second aspect of the invention, in the humidity detecting device, wherein the switching unit uses a switchable upper limit frequency value corresponding to one of the first frequency and the second frequency, and wherein the switching unit uses a switchable lower limit frequency value corresponding to another one of the first frequency and the second frequency.

According to a third aspect of the invention, in the humidity detecting device, wherein the discriminating unit discriminates the humidity sensor by comparing a predetermined discrimination criterion with the at least one of the difference and the change rate between the first impedance and the second impedance, and wherein the humidity detecting device further comprises a changing unit that changes the discrimination criterion according to at least one of the ambient temperature detected by the temperature sensor and the humidity detected by the humidity sensor.

According to a fourth aspect of the invention, in the humidity detecting device, wherein the applying unit comprises: a first applying part that applies the AC voltage to one end of the humidity sensor; a second applying part, which comprises a first resistor connected to the other end of the humidity sensor and having a first resistance value, and which applies a voltage with a phase opposite to that of a voltage applied by the first applying part to the other end of the humidity sensor; and a third applying part, which comprises a second resistor connected to the other end of the humidity sensor and having a second resistance value that is different from the first resistance value, and which applies a voltage with a phase opposite to that of a voltage applied by the first applying part to the other end of the humidity sensor, and wherein the control unit selects one of the second applying part and the third applying part according to the discriminated humidity sensor.

According to a fifth aspect of the invention, the humidity detecting device further comprises: a storage unit that stores a plurality of temperature correction tables corresponding to the discriminated humidity sensor, each of the plurality of temperature correction tables associating data of the humidity detection signal with detected humidity data according to the detected ambient temperature, wherein the control unit reads the detected humidity data corresponding to the humidity detection signal data out of the temperature correction table corresponding to the discriminated humidity sensor among the plurality of temperature correction tables.

According to a sixth aspect of the invention, the humidity detecting device further comprises: a storage unit that stores a criterion temperature correction table for associating data of the humidity detection signal with detected humidity data according to the detected ambient temperature, wherein the control unit alters the detected humidity data read out of the criterion temperature correction table according to the discriminated humidity sensor.

According to a seventh aspect of the invention, in the humidity detecting device, wherein, when the at least one of the difference and the change rate between the first impedance and the second impedance is equal to or less than a predetermined value, the discriminating unit judges that an abnormality occurs in the humidity detecting device and generates a notification signal for notifying the abnormality.

According to an eighth aspect of the invention, there is provided an image forming apparatus comprising: a humidity detecting device comprising: a humidity sensor, which detects humidity using a change in an impedance by humidity, and which generates a humidity detection signal according to application of an AC voltage; an applying unit that applies the AC voltage to the humidity sensor; a detecting unit that detects the impedance of the humidity sensor based on the humidity detection signal; a switching unit that switches a frequency of the AC voltage to at least a first frequency and a second frequency that is different from the first frequency, the impedance of the humidity sensor being a first impedance at the first frequency, the impedance of the humidity sensor being a second impedance at the second frequency; a temperature sensor that detects ambient temperature of the humidity sensor; a calculating unit that uses detected values of the first impedance and the second impedance detected by the detecting unit so as to calculate at least one of a difference and a change rate between the first impedance and the second impedance; a discriminating unit that discriminates the humidity sensor based on the at least one of the difference and the change rate between the first impedance and the second impedance; and a control unit that performs processing corresponding to the discriminated humidity sensor when the humidity detecting device detects the humidity; an image forming unit that forms an image on a sheet based on image data; and an apparatus control unit that controls image forming processing of the image forming unit based on the humidity detected by the humidity detecting device.

According to the aspects of the invention, a kind of a humidity sensor can be discriminated based on a difference between impedances and/or a change rate of the impedance of the humidity sensor simply, and processing according to the kind of the humidity sensor, for example, selection of an AC voltage applying part adapted to the humidity sensor can be made. That is, the kind of the humidity sensor can easily be discriminated and appropriate processing according to the kind of the humidity sensor can be performed. Further, humidity sensors with different characteristics can be used in a common circuit substrate and flexibility in use of a component improves, and availability of the component improves. Incidentally, in the aspects of the invention, the term "impedance" is used in a meaning of resistance, but a reactance component is not included therein.

According to the second aspect of the invention, predetermined temperature and predetermined humidity have characteristics in which a difference between impedances of a humidity sensor becomes large as a range of a driving frequency is wide. Therefore, a kind of the humidity sensor can efficiently be discriminated by a difference between impedances or a change rate of the impedance based on impedance measurement in switchable frequency upper limit value and lower limit value.

According to the third aspect of the invention, by discriminating a humidity sensor based on a predetermined discrimination criterion, it is possible to perform the discrimination more appropriately. Further, when a difference between impedances and/or a change rate of the impedance of the humidity sensor depends on ambient temperature and/or humidity, for example, a discrimination criterion table corresponding to the ambient temperature and/or humidity is provided and the discrimination criterion is changed according to the ambient temperature and/or humidity with reference to the discrimination criterion table and thereby, a kind of the humidity sensor can be discriminated with high accuracy.

According to the fourth aspect of the invention, humidity can be detected with high accuracy since an applying part adapted to a humidity sensor can be selected according to a difference between impedances and/or a change rate of the impedance of the humidity sensor.

According to the fifth aspect of the invention, temperature correction processing according to a discriminated humidity sensor can be performed, and humidity can be detected with high accuracy.

According to the sixth aspect of the invention, the storage unit can effectively be used since it is unnecessary to store a temperature correction table corresponding to each of the humidity sensors.

According to the seventh aspect of the invention, abnormality in a humidity detecting device such as a peripheral circuit or a humidity sensor is detected by a difference between impedances and/or a change rate of the impedance and a user can be notified of the abnormality by, for example, supplying a notification signal to an internal or external notification device.

According to the ninth aspect of the invention, in a humidity detecting device in an image forming apparatus, a kind of a humidity sensor can easily be discriminated and appropriate processing according to the kind of the humidity sensor can be performed. Therefore, predetermined quality of a formed image can be ensured even in the case of using the humidity sensors having different characteristics. Further, the humidity sensors with different characteristics can be used in a common circuit substrate. Therefore, it is possible to improve flexibility in use of components and availability of the components.

According to a humidity detecting device of the invention, a kind of a humidity sensor can easily be discriminated and appropriate processing according to the kind of the humidity sensor can be performed.

<Exemplary Embodiments>

Exemplary embodiments of the invention will now be described with reference to the drawings.

<First Exemplary Embodiment>
(Humidity Detecting Device)

Figure 1:
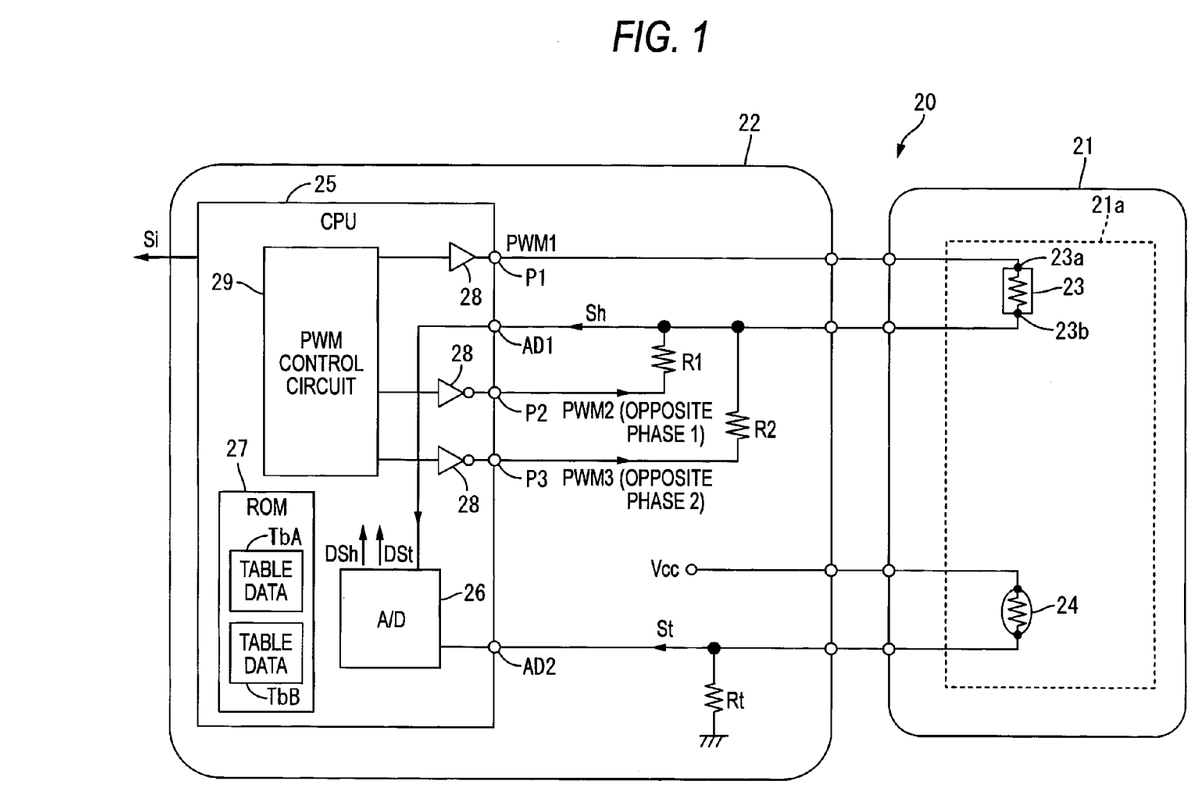
FIG. 1 is a schematic circuit diagram of a humidity detecting device according to a first exemplary embodiment of the invention.

A humidity detecting device according to a first exemplary embodiment of the invention will be described with reference to FIGS. 1 to 9. FIG. 1 shows a schematic circuit configuration of a humidity detecting device 20 of the first exemplary embodiment. The humidity detecting device 20 broadly includes a detecting part 21 for detecting humidity and a control part 22 for controlling the detecting part 21 as shown in FIG. 1.

The detecting part 21 includes, for example, a humidity sensor 23 which is formed on the same sensor substrate 21a and detects humidity and generates a humidity detection signal Sh, and a temperature sensor 24 (for example, a thermistor) which detects ambient temperature of the humidity sensor 23 and generates a temperature detection signal St.

Here, a polymeric (water-soluble) humidity sensor is preferably used as the resistance variable type humidity sensor 23. That is because, the polymeric (water-soluble) humidity sensor is low in cost, and also humidity can suitably be detected even in a high-humidity environment since a humidity detection range is wide. Further, that is because a difference between impedances by a difference between frequencies (driving frequencies) of an applied AC voltage tends to occur as described below.

The control part 22 includes a CPU (one example of a detecting unit, a calculating unit, a discriminating unit, a control unit, and a switching unit) 25 for applying an AC voltage to the humidity sensor 23. The CPU 25 applies an AC voltage to the humidity sensor 23 as the power source voltage since the humidity sensor 23 requires AC driving from the characteristics at the time of detecting humidity. The CPU 25 applies a first PWM signal PWM1 to a first terminal 23a of the humidity sensor through a first PWM port (first applying part) P1 in order to apply the AC voltage. Here, the CPU 25 is, for example, an ASIC (application specific integrated circuit).

Figure 2:
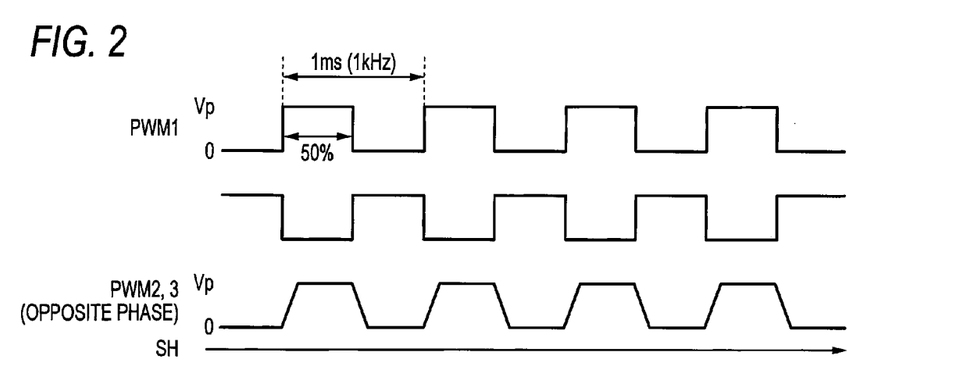
FIG. 2 is a time chart according to humidity detection in the first exemplary embodiment.

The CPU 25 applies a second PWM signal PWM2 or a third PWM signal PWM3 with a phase opposite to that of the first PWM signal PWM1 to a second terminal (one example of the other end) 23b of the humidity sensor through a second PWM port (one example of a second applying part) P2 or a third PWM port (one example of a third applying part) P3 in order to apply the AC voltage to the humidity sensor 23 (see FIG. 2). That is, the humidity sensor 23 is driven on AC by a combined signal of the first PWM signal PWM1 and the second PWM signal PWM2 or by a combined signal of the first PWM signal PWM1 and the third PWM signal PWM3. In addition, the first PWM signal PWM1, the second PWM signal PWM2 and the third PWM signal PWM3 are respectively outputted through output buffers 28. In addition, a waveform example of the first PWM signal PWM1, the second and third PWM signals (PWM2, PWM3) and the humidity detection signal Sh is shown in a time chart of FIG. 2. Here, a frequency of the first PWM signal PWM1, the second and third PWM signals (PWM2, PWM3) is 1 kHz and a pulse duty ratio is 50%.

The control part 22 also includes a first detection resistor R1, a temperature detection resistor Rt and a second detection resistor R2. The first detection resistor R1 is connected between the second PWM port P2 and the second terminal 23b of the humidity sensor and generates the humidity detection signal (voltage signal) Sh by voltage dividing between the resistor R1 and resistance (impedance) of the humidity sensor 23. The temperature detection resistor Rt is connected between the temperature sensor 24 and a ground and generates the temperature detection signal (voltage signal) St by voltage dividing of a power source Vcc between the resistor Rt and resistance by the temperature sensor 24. The second detection resistor R2 is connected between the third PWM port P3 and the second terminal 23b of the humidity sensor and generates the humidity detection signal Sh and has a resistance value different from a resistance value of the first detection resistor R1. In addition, the resistance values of the first detection resistor R1 and the second detection resistor R2 are properly decided according to an impedance of the discriminated humidity sensor 23. Here, the resistance value of the first detection resistor R1 is smaller than the resistance value of the second detection resistor R2.

The CPU 25 also includes an A/D conversion circuit 26. The A/D conversion circuit 26 receives the humidity detection signal Sh through a first AD port AD1 and generates a humidity read value DSh which is a digital value according to the humidity detection signal Sh. The A/D conversion circuit 26 also receives the temperature detection signal St through a second AD port AD2 and generates a temperature read value DSt which is a digital value according to the temperature detection signal St. The CPU 25 performs processing according to humidity detection based on the humidity read value DSh and the temperature read value DSt.

Further, the CPU 25 also includes ROM (one example of a storage unit) 27 that stores temperature correction tables TbA and TbB according to humidity detection, a control program according to humidity detection, etc. Then, the CPU 25 obtains detected humidity data according to ambient temperature based on the humidity read value DSh and the temperature read value DSt using the temperature correction tables TbA and TbB.

The CPU 25 also includes a PWM control circuit (one example of an applying unit and a switching unit) 29. The PWM control circuit 29 generates the first to third PWM signals (PWM1, PWM2, PWM3) and also switches frequency of the first to third PWM signals. Also, the PWM control circuit 29 selects any one of the second and third PWM ports (P2, P3) according to the discriminated sensor.

(Discrimination Action of Humidity Sensor)

Next, a discrimination action of the humidity sensor 23 by the humidity detecting device 20 will be described with reference to FIGS. 3 to 9.

Figure 3:
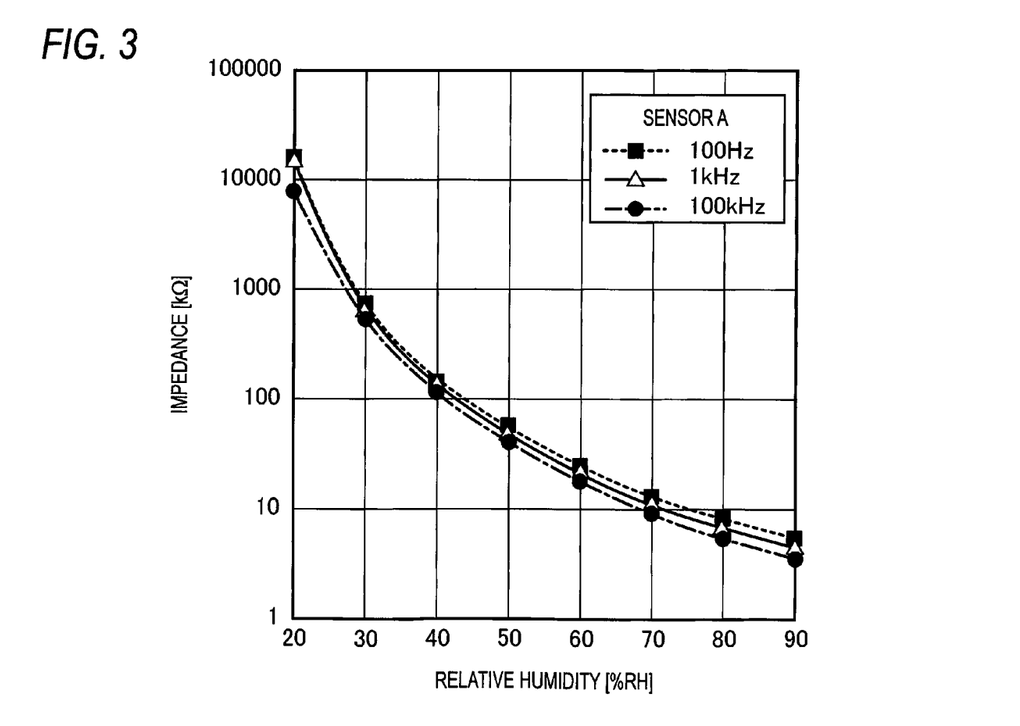
FIG. 3 is a graph showing a relation between humidity and an impedance of a humidity sensor by a difference between driving frequencies.
Figure 4:
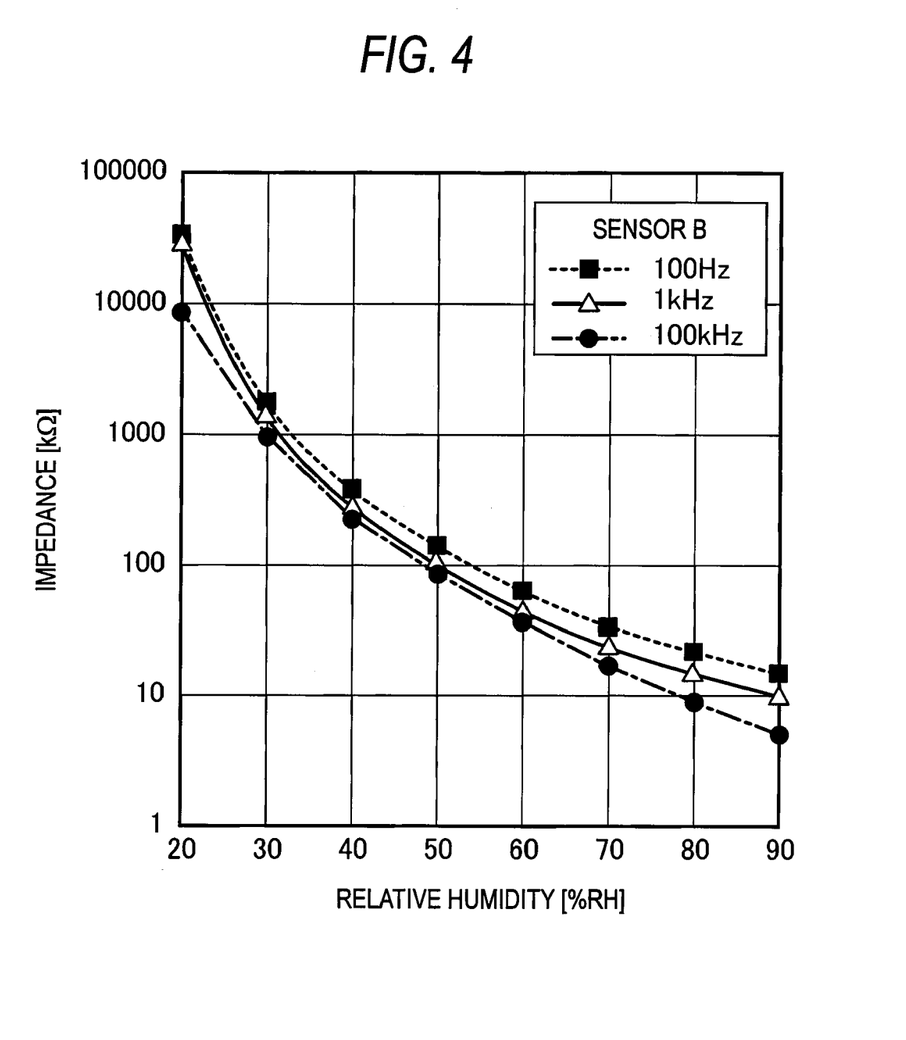
FIG. 4 is a graph showing a relation between humidity and an impedance of another humidity sensor at plural driving frequencies.

FIG. 3 is a graph showing a relation between humidity and an impedance Rz of a polymeric (water-soluble) humidity sensor A by a difference between frequencies (100 Hz, 1 kHz, 100 kHz) of an applied AC voltage (PWM signal). Also, FIG. 4 is a graph showing a relation between humidity and an impedance Rz of a polymeric (water-soluble) humidity sensor B by a difference between frequencies of an applied AC voltage similarly. As shown in FIGS. 3 and 4, an impedance-humidity curve according to each of the frequencies of the applied AC voltage varies depending on a kind of the polymeric (water-soluble) humidity sensor. Therefore, in the first exemplary embodiment, the sensors with different kinds, for example, different makers are discriminated using a difference in each of the impedance-humidity curves in the humidity sensor.

More concretely, a difference between a first detected value of an impedance Rz at a high frequency (corresponding to a "first frequency" or a "second frequency" in the invention) and a second detected value of an impedance Rz at a low frequency (corresponding to a "second frequency" or a "first frequency" in the invention) is calculated and the humidity sensor is discriminated based on the difference between the impedances Rz.

In addition, the humidity sensor 23 using the impedances Rz of the humidity sensor 23 at different driving frequencies can also be discriminated based on a change rate of the impedance Rz or the difference between the impedances Rz and the change rate of the impedance Rz as well as the difference between the impedances Rz.

In addition, the impedance (resistance) Rz of the humidity sensor 23 is represented by the following formula 1 in the case of assuming that a voltage value of the humidity detection signal Sh is Vd1 and a voltage value of a PWM signal is Vp and a resistance value of the first detection resistor is R1 and the second PWM port P2 is selected.

$$Rz = ((Vp - Vd1)/Vd1)R1 \quad \text{Formula 1}$$

The impedance Rz is calculated from the voltage value Vd1 of the humidity detection signal Sh since Vp and R1 are known herein. That is, there is a correspondence relation between the impedance Rz of the humidity sensor 23 and the voltage value Vd1 (detected humidity) of the humidity detection signal Sh, and the CPU (one example of a detecting unit) 25 detects the impedance Rz based on the humidity detection signal Sh. Specifically, the CPU 25 detects the impedance Rz by calculating the impedance Rz according to the formula 1.

Also, the humidity sensor 23 is not necessarily limited to the polymeric (water-soluble) humidity sensor herein. For example, the humidity sensor 23 may be a humidity sensor with a difference between the impedances Rz according to a frequency of an applied AC voltage in brief.

Figure 5:
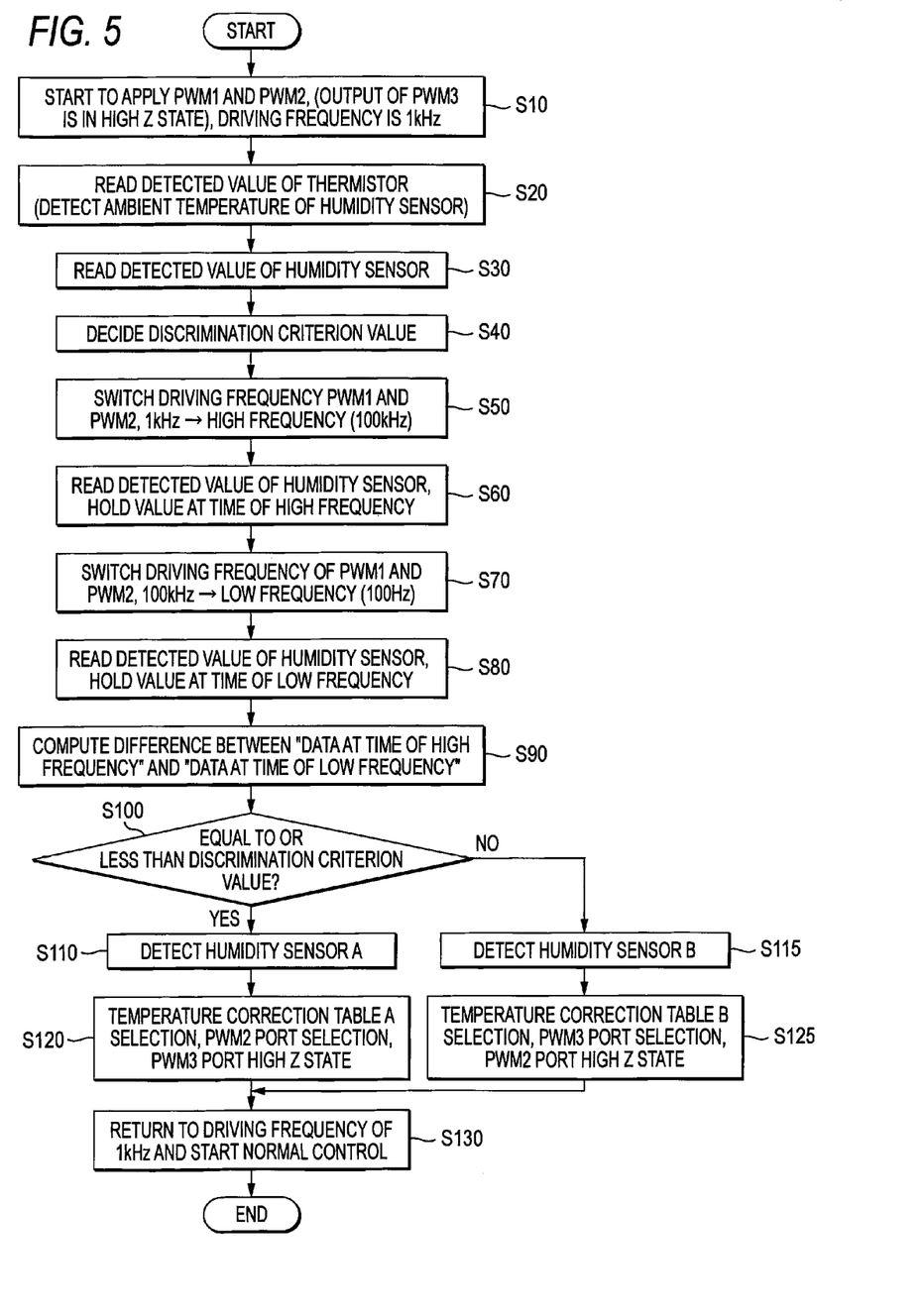
FIG. 5 is a flowchart showing a flow of discrimination processing of a humidity sensor.

Processing of sensor discrimination in the first exemplary embodiment will be described below in detail with reference to a flowchart of FIG. 5. FIG. 5 is the flowchart showing a flow of processing according to discrimination of the humidity sensor by the first exemplary embodiment. The processing of sensor discrimination is executed by the CPU 25 according to a predetermined processing program. The processing of sensor discrimination is started with supply of a power source to the humidity detecting device 20.

In step S10 of FIG. 5, the CPU 25, specifically, the PWM control circuit 29 applies the first PWM signal PWM1 and the second PWM signal PWM2 with a frequency of 1 kHz which is a frequency at the time of detecting normal humidity to the humidity sensor 23. At this time, the third PWM port P3 is set in a high impedance state. Then, in step S20, the CPU 25 reads the temperature detection signal St from the temperature sensor 24 and detects ambient temperature of the humidity sensor 23.

Then, in step S30, the humidity detection signal Sh is read from the humidity sensor 23 and ambient humidity of the humidity sensor 23 is detected. Then, in step S40, the CPU 25 decides a discrimination criterion value DZ from the detected temperature and humidity. In that case, the CPU 25 decides the discrimination criterion value DZ with reference to, for example, discrimination criterion table data indicating correspondence between the discrimination criterion value and the temperature and humidity. Here, the discrimination criterion value DZ is a criterion value for discriminating the humidity sensor 23 by a difference between the time of a low frequency and the time of a high frequency of the impedances Rz of the humidity sensor 23 as described below. In addition, the discrimination criterion table data is stored in, for example, the ROM 27.

Then, in step S50, the CPU 25 switches the frequencies of the first PWM signal PWM1 and the second PWM signal PWM2 from 1 kHz of the normal frequency to, for example, 100 kHz of a high frequency. Here, the frequency of 100 kHz is an upper limit value capable of being switched by the CPU 25, specifically, the PWM control circuit 29. Then, in step S60, the humidity detection signal Sh at the time of the high frequency is read, and humidity (voltage value) at the time of the high frequency is held.

In step S70, the CPU 25 switches the frequencies of the first PWM signal PWM1 and the second PWM signal PWM2 from 100 kHz to, for example, 100 Hz of a low frequency. Here, the frequency of 100 Hz is a lower limit value capable of being switched by the CPU 25. Then, in step S80, the humidity detection signal Sh at the time of the low frequency is read and, humidity (voltage value) at the time of the low frequency is held.

Then, in step S90, a difference between "data at the time of the high frequency" and "data at the time of the low frequency" is calculated. Here, "data" is set at the impedance Rz of the humidity sensor 23 calculated from the humidity detection signal Sh by the formula 1. That is, in step S90, the CPU 25 calculates the difference between the time of the high frequency and the time of the low frequency of the impedances Rz of the humidity sensor 23. Then, in step S100, it is determined whether or not the difference between the impedances Rz is the discrimination criterion value DZ or more.

Figure 6:
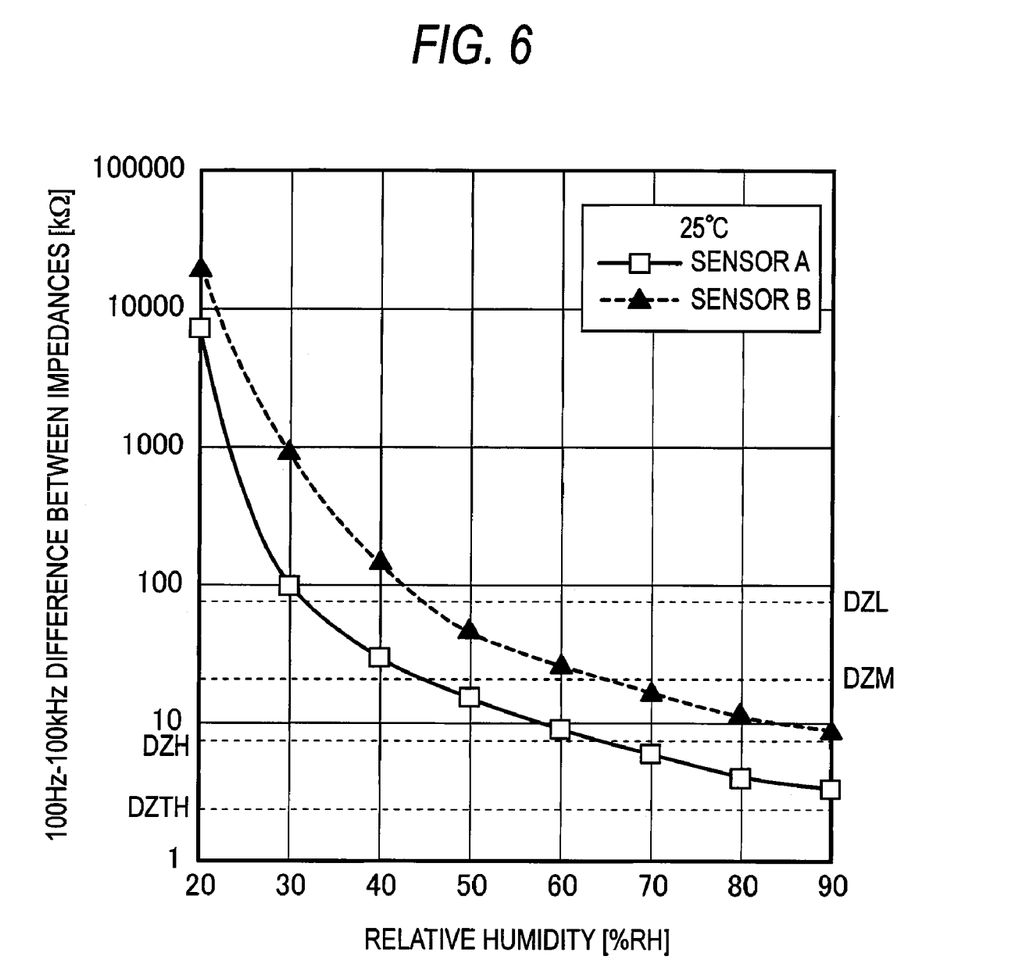
FIG. 6 is a graph showing a relation between humidity and a difference between impedances of humidity sensors in two kinds of humidity sensors.

In addition, the discrimination criterion value DZ varies depending on ambient temperature and ambient humidity as described above. Examples of variation of the discrimination criterion value DZ will be described with reference to FIGS. 6 to 8. FIG. 6 is a graph schematically illustrating a relation between relative humidity and a difference between impedances Rz of two kinds of humidity sensor A and sensor B at ambient temperature of, for example, 25° C. Here, for example, an example in which a discrimination criterion value is set at DZL in a low humidity region and a discrimination criterion value is set at DZM in a middle humidity region and a discrimination criterion value is set at DZH in a high humidity region is shown. In addition, a setting form of the discrimination criterion value by ambient humidity is not limited thereto. The setting form of the discrimination criterion value may be properly set according to frequency characteristics of the impedance of the humidity sensor discriminated.

Figure 7:
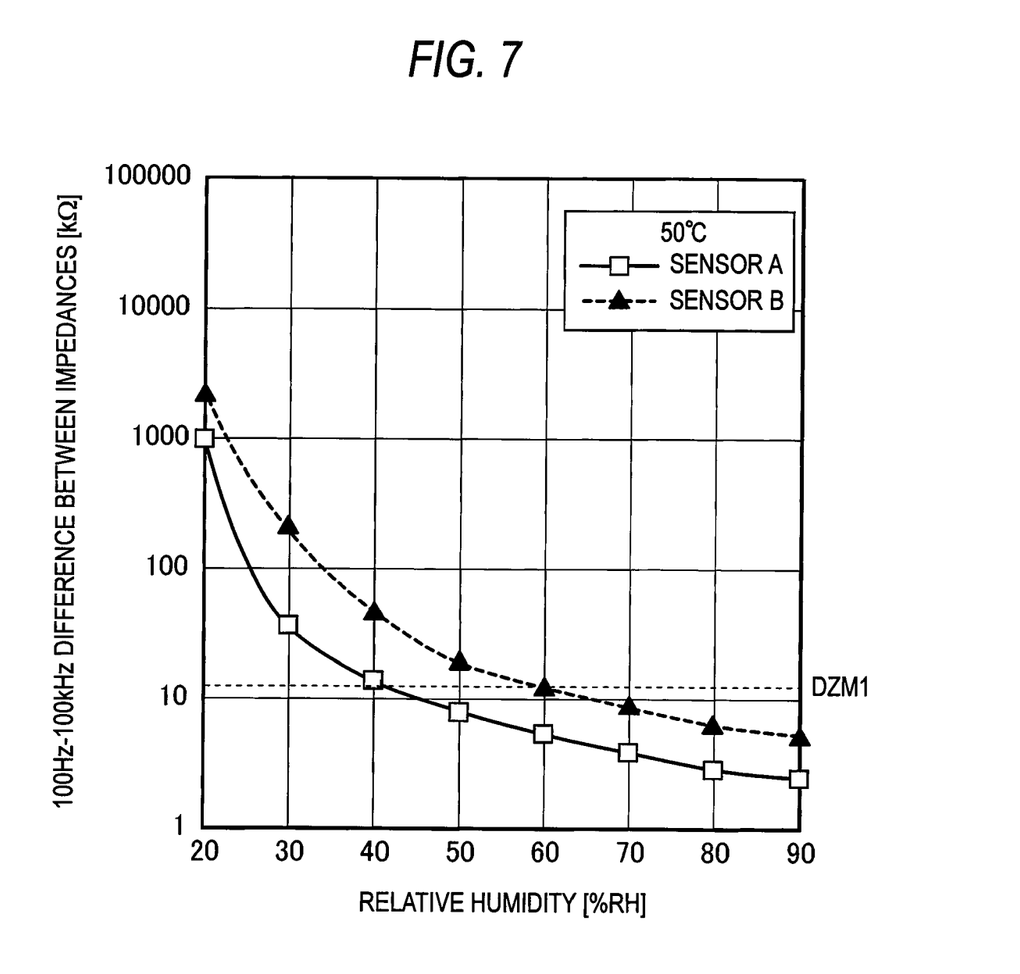
FIG. 7 is a graph schematically showing a relation between humidity and a difference between impedances of humidity sensors when ambient temperature is high in FIG. 6.
Figure 8:
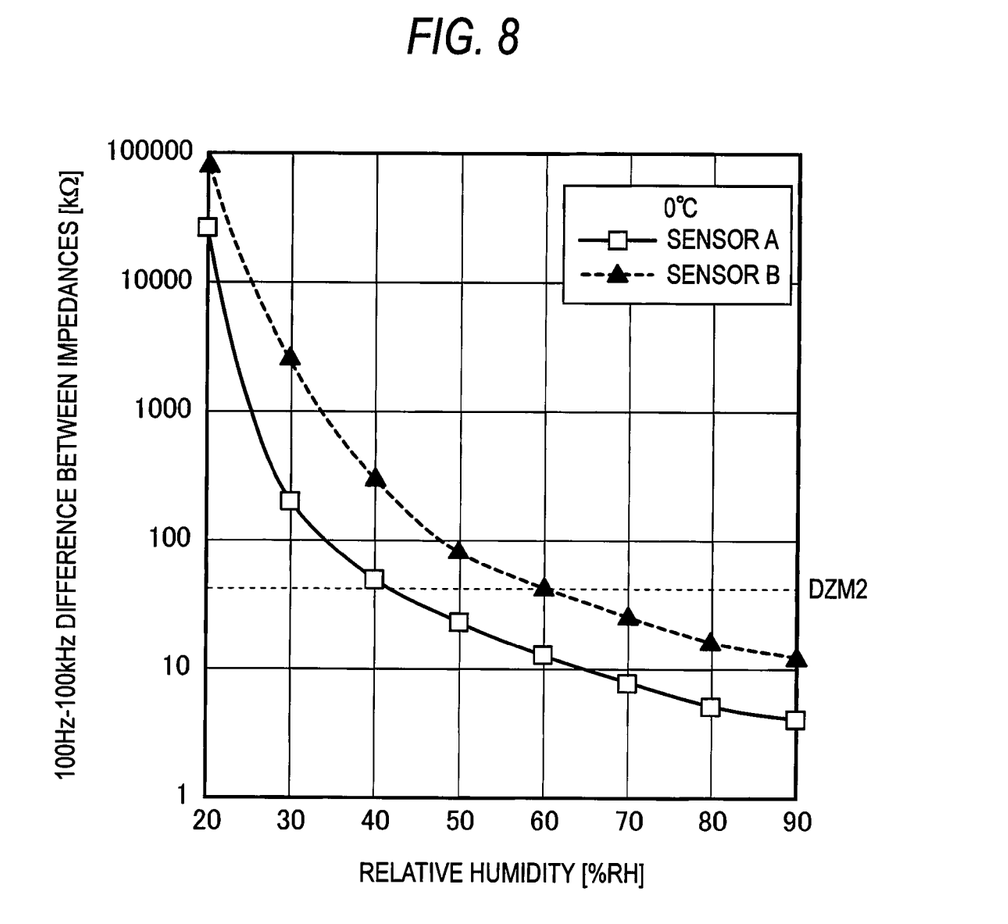
FIG. 8 is a graph showing a relation between humidity and a difference between impedances of humidity sensors when ambient temperature is low in FIG. 6.

FIG. 7 is a graph schematically illustrating a relation between relative humidity and a difference between impedances Rz of humidity sensors A and B at ambient temperature of 50° C. Here, only a discrimination criterion value DZM1 of a middle humidity region is shown. Also, FIG. 8 is a graph schematically illustrating a relation between relative humidity and a difference between impedances Rz of humidity sensors A and B at ambient temperature of 0° C. Here, only a discrimination criterion value DZM2 of a middle humidity region is also shown.

If it is determined that the difference between the impedances Rz is equal to or less than the discrimination criterion value DZ in step S100 (S100: YES), for example, if it is determined that the difference between the impedances Rz is equal to or less than the discrimination criterion value DZM in the case of assuming that temperature is 25° C. and humidity is 50%, the CPU 25 detects that the humidity sensor 23 is a sensor A shown in FIG. 6 in step S110 (see FIG. 6). Then, in step S120, the CPU 25 selects the temperature correction table TbA and the second PWM port P2 and sets the third PWM port P3 in a high impedance state.

Then, in step S130, the CPU 25 returns the frequencies of the first PWM signal PWM1 and the second PWM signal PWM2 to 1 kHz of the normal frequency and starts normal humidity detection. In addition, the first detection resistor R1 has a resistance value smaller than that of the second detection resistor R2 as described above. That is because the impedance Rz of the sensor A is smaller than the impedance Rz of the sensor B (see FIGS. 3 and 4). That is, this purpose is to suppress variations in a value of the humidity detection signal (voltage signal) Sh by a difference between the impedances Rz of the sensor A and the sensor B and obtain predetermined detection sensitivity without depending on the sensor.

In contrast, if it is determined that the difference between the impedances Rz is not equal to or less than the discrimination criterion value DZ in step S100 (S100: NO), for example, if it is determined that the difference between the impedances Rz is not equal to or less than the discrimination criterion value DZM in the case of assuming that temperature is 25° C. and humidity is 50%, the CPU 25 detects that the humidity sensor 23 is a sensor B shown in FIG. 6 in step S115 (see FIG. 6). Then, in step S125, the CPU 25 selects the temperature correction table TbB and the third PWM port P3 and sets the second PWM port P2 in a high impedance state. Then, a return to normal control is made in step S130.

Incidentally, the temperature correction tables TbA and TbB are previously created in correspondence with the sensor A and the sensor B discriminated and are stored in, for example, the ROM 27. Also, selection of the second PWM port P2 and the third PWM port P3, that is, values of the voltage dividing resistors R1 and R2 are previously decided so as to obtain predetermined detection sensitivity in correspondence with characteristics of the sensor A and the sensor B.

Figure 9:
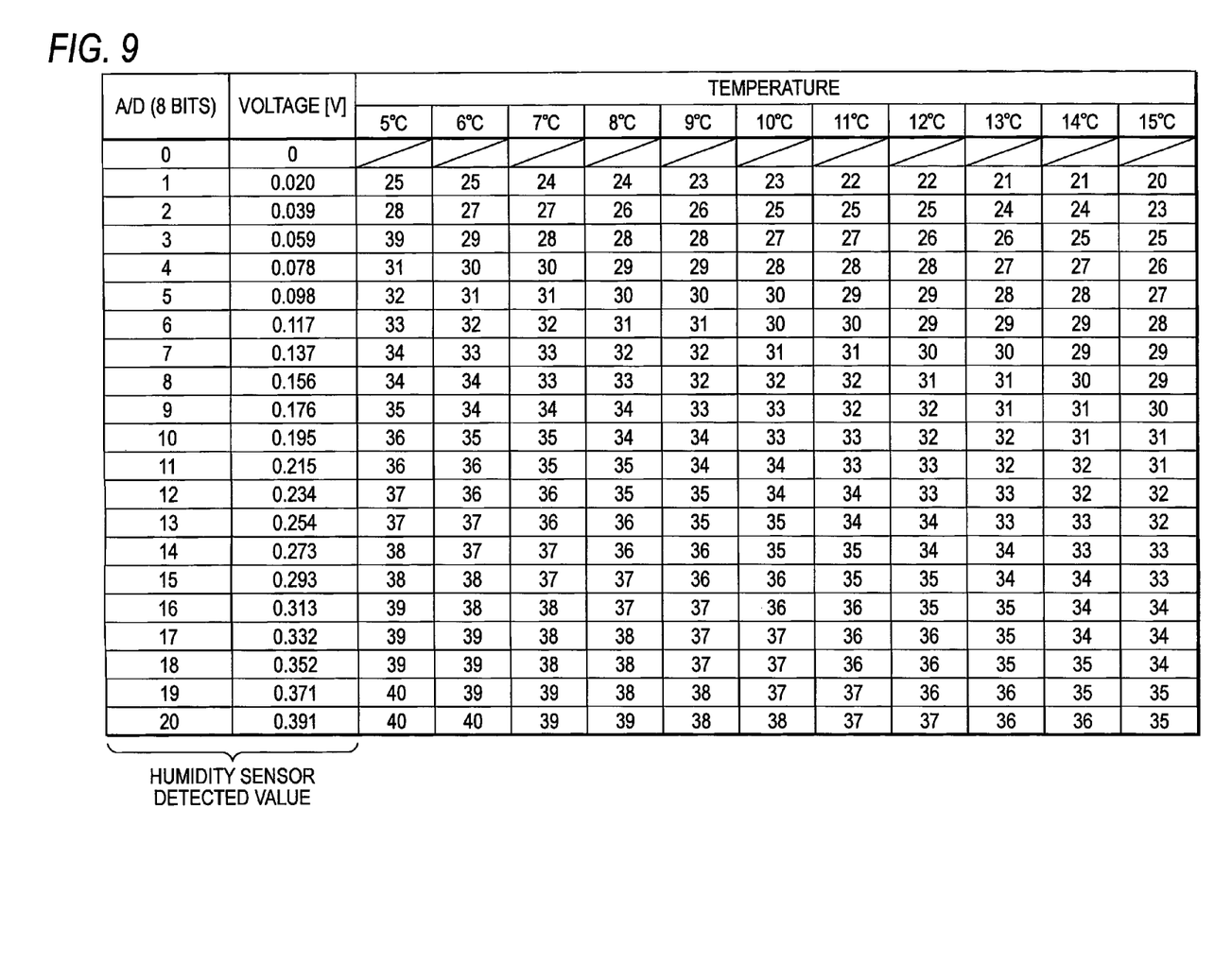
FIG. 9 is a table showing one example of a temperature correction table.

FIG. 9 shows a part of an example of the temperature correction table Tb. The CPU 25 reads detected humidity data corresponding to the humidity read value (detected voltage) DSh and the temperature read value DSt out of the temperature correction table Tb, and sets the detected humidity data read out at detected humidity. That is, the humidity read value (detected voltage) DSh is not set at the detected humidity as it is, and is set at the detected humidity by data according to ambient temperature using the temperature correction table Tb.

Incidentally, the number of the kinds of the discriminated humidity sensor 23 is not limited to two. For example, three kinds or four kinds of humidity sensors may also be discriminated. In that case, three kinds or four kinds of temperature correction tables may be provided according to characteristics of the humidity sensors, and a fourth PWM port, a fifth PWM port, a third voltage dividing resistor and a fourth voltage dividing resistor may be further provided. Also, it may be configured such that two kinds or three kinds of discrimination criterion values DZ are provided. Further, in the case of discriminating two kinds or more of humidity sensors, the first detection resistor R1 may be formed by a digital potentiometer, and a voltage dividing resistor corresponding to the discriminated humidity sensor may be configured by adjustment of the digital potentiometer. According thereto, the structure of the voltage dividing resistor can be simplified.

Also, only one criterion temperature correction table Tb may be stored in the ROM 27 instead of storing plural temperature correction tables Tb corresponding to the discriminated sensor. In this case, the CPU 25 alters temperature correction data read out of the criterion temperature correction table Tb according to the discriminated humidity sensor and sets the altered temperature correction data at detected humidity. As an example of altering the temperature correction data in this case, for example, predetermined humidity (for example, 1% or 2%) according to the discriminated humidity sensor is added to or subtracted from the temperature correction data (humidity data) read out. In that case, it may be configured so as to change the added or subtracted predetermined humidity according to a detected humidity region.

A kind of the humidity sensor 23 can easily be discriminated based on a difference between impedances of the humidity sensor 23 at different driving frequencies simply. Then, processing according to the kind of the discriminated humidity sensor 23, that is, selection of a temperature correction table and selection of a detection resistor adapted to the discriminated humidity sensor 23 can be made. Therefore, appropriate processing according to the kind of the humidity sensor 23 can be performed and humidity can be detected with high accuracy. Further, plural humidity sensors 23 with different impedance frequency characteristics can be used in the common circuit substrate 21a. Therefore, it is possible to improve flexibility in the used humidity sensor 23 and availability of the humidity sensor 23.

Predetermined temperature and predetermined humidity have characteristics in which a difference between impedances of the humidity sensor 23 becomes large as a range of a driving frequency is wide, that is, a difference between the driving frequencies is large. Therefore, a kind of the humidity sensor can efficiently be discriminated by using the impedance difference based on impedances in switchable frequency upper limit value (100 kHz) and lower limit value (100 Hz).

Since the humidity sensor 23 is discriminated based on predetermined discrimination criteria (DZL, DZM, DZH), it is possible to perform the discrimination more appropriately. Further, since the discrimination criteria (DZL, DZM, DZH) are changed according to ambient temperature, a kind of the humidity sensor can be discriminated with high accuracy.

<Second Exemplary Embodiment>

Figure 10:
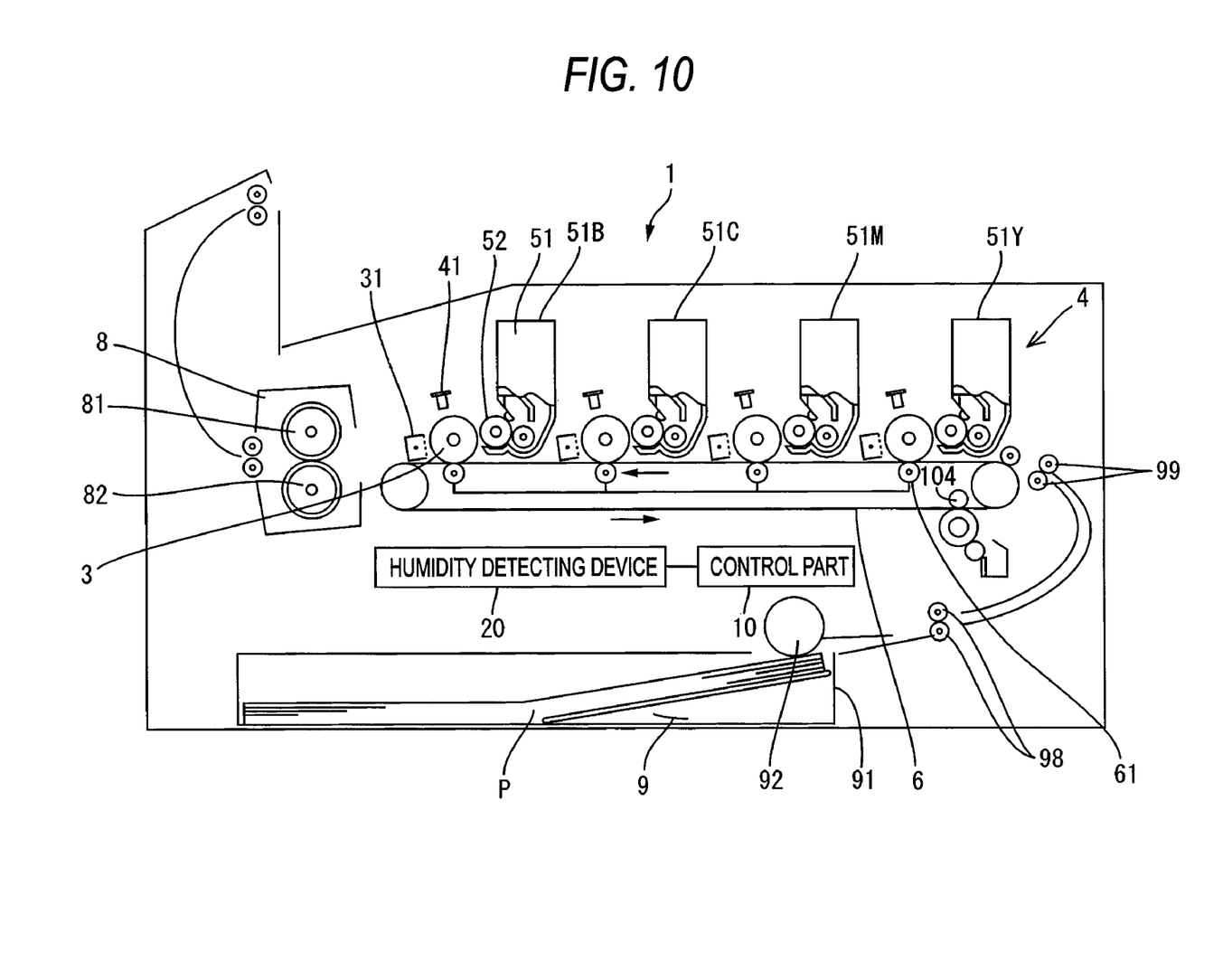
FIG. 10 is a schematic diagram of an image forming apparatus according to a second exemplary embodiment of the invention.

An image forming apparatus according to a second exemplary embodiment of the invention will be described with reference to FIG. 10. FIG. 10 is a schematic sectional diagram of an image forming apparatus 1. Incidentally, the image forming apparatus 1 may be, for example, a color laser printer, an LED printer, a monochrome printer or the so-called complex machine including a copy function, etc.

The image forming apparatus 1 illustrated in FIG. 10 includes a toner image forming part (one example of an image forming unit) 4, a sheet conveying belt 6, a fixing part 8, a feeder unit 9, an image forming apparatus control part (one example of an apparatus control unit) 10 and a humidity detecting device 20, etc., and an image of four colors according to image data inputted from the outside is formed on a sheet P as a print medium. Here, the humidity detecting device 20 is the humidity detecting device described in the first exemplary embodiment.

Then, the toner image forming part 4 includes four developing units 51Y, 51M, 51C, 51B in which toner of yellow, magenta, cyan and black is respectively accumulated, four photosensitive drums 3, four chargers 31 for uniformly charging the photosensitive drums 3, and four scanner units 41 for exposing surfaces of the photosensitive drums 3 after charging by, for example, laser light and forming an electrostatic latent image according to image data. In addition, in the scanner units 41, most of the illustration is omitted and only the portion in which the laser light is finally emitted is illustrated.

The developing units 51Y, 51M, 51C, 51B respectively include developing rollers 52 for supplying toner to the photosensitive drums 3, and develop a toner image to the electrostatic latent image formed on the photosensitive drums 3.

The feeder unit 9 includes a receiving tray 91 for receiving a sheet P and a pickup roller 92 for delivering the sheet (object) P. Then, the sheet P received in the receiving tray 91 is taken out of the feeder unit 9 one by one by the pickup roller 92 and is fed to the sheet conveying belt 6 through conveying rollers 98 and registration rollers 99.

In the vicinity of a position opposed to each of the photosensitive drums 3, transfer rollers 61 are respectively provided in a state of sandwiching the sheet conveying belt 6. Then, in the sheet conveying belt 6, the surface of the side opposed to the photosensitive drums 3 moves from a right direction in the diagram to a left direction in the diagram as shown in FIG. 10 and the sheet P fed from the registration rollers 99 is sequentially conveyed between the photosensitive drums 3 and the sheet conveying belt 6 and is fed to the fixing part 8.

In the transfer rollers 61, a transfer bias (for example, −10 to −11 µA, maximum of 6 kV as a voltage) with a polarity opposite to a charging polarity of toner is applied between the transfer rollers 61 and the photosensitive drums 3 by a high-voltage control apparatus (not shown) and a toner image formed on the photosensitive drums 3 is transferred to the sheet P conveyed by the sheet conveying belt 6.

The fixing part 8 includes a heating roller 81 and a pressing roller 82. The sheet P, to which a toner image is transferred, is heated and pressed while being pinched and conveyed by the heating roller 81 and the pressing roller 82. Accordingly, the toner image is fixed on the sheet P.

The image forming apparatus control part 10 includes a control apparatus, etc., using a CPU (not shown), and performs control of the whole action of the image forming apparatus 1. The image forming apparatus control part 10 controls image forming processing of the toner image forming part 4 based on humidity detected by the humidity detecting device 20. Concretely, for example, a bias for charging toner in the toner image forming part 4 is controlled according to detected humidity and the amount of supply of toner from the developing units 51 to the photosensitive drums 3 is controlled according to humidity. Alternatively, a transfer bias applied to the transfer rollers 61 is controlled according to detected humidity and a toner image is well transferred to the sheet P without depending on humidity. That is, the image forming apparatus control part 10 maintains predetermined quality of a formed image without depending on humidity based on humidity detected by the humidity detecting device 20.

Therefore, according to the configuration of the second exemplary embodiment, an effect similar to that of the first exemplary embodiment can be obtained in the humidity detecting device 20 in the image forming apparatus 1. Accordingly, quality of a formed image can be ensured even in the case of using the humidity sensors 23 having different characteristics in the image forming apparatus 1.

<Other Exemplary Embodiments>

The invention is not limited to the above-described exemplary embodiments. For example, the following embodiments are included in the technical scope of the invention.

In the above-described exemplary embodiments, the example in which the CPU 25 discriminates the humidity sensor 23 based on a difference between impedances calculated has been shown. However, the invention is not limited thereto. For example, the humidity sensor 23 may be discriminated based on a change rate of impedances detected at high and low frequencies, or the difference between the impedances and the change rate of the impedances.

Figure 11:
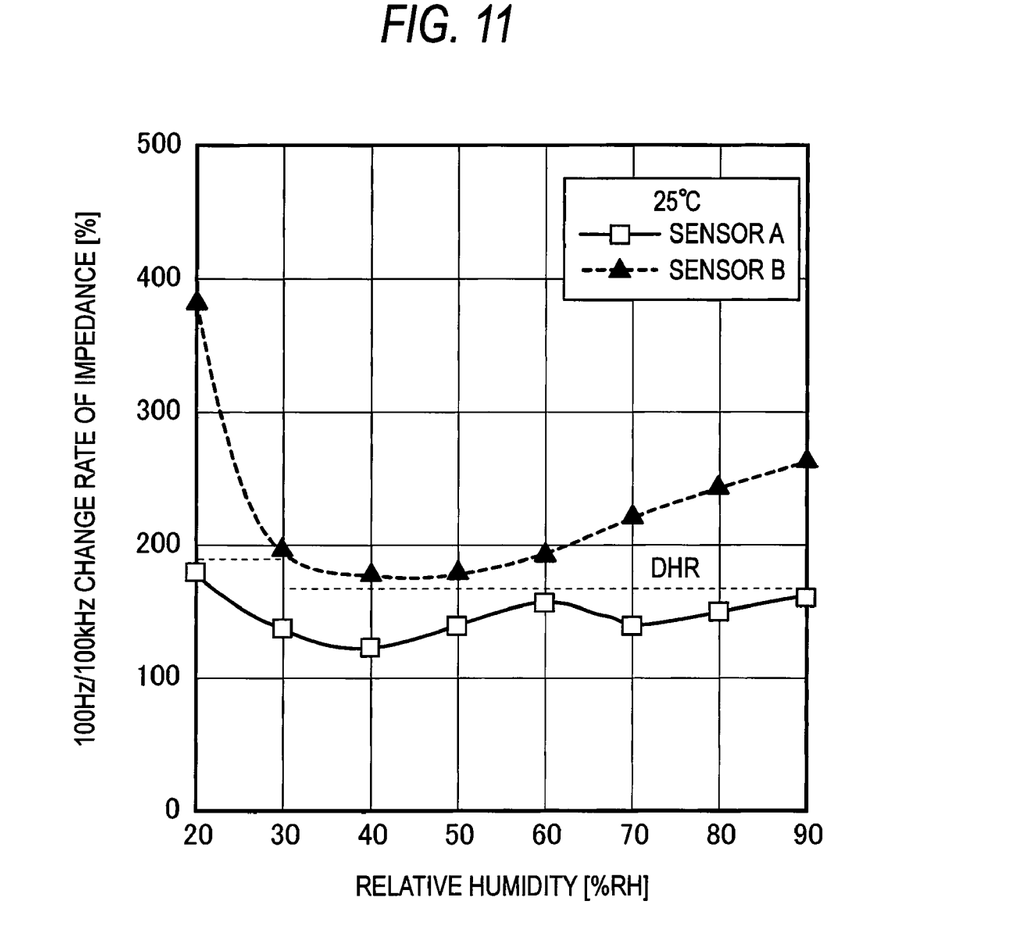
FIG. 11 is a graph showing a relation between humidity and a change rate of impedances of humidity sensors in two kinds of humidity sensors.

For example, FIG. 11 is a diagram shown by changing a difference between impedances in FIG. 6 into a change rate (percentage; %) of the impedance. There is a difference between a sensor A and a sensor B even in the case of being shown by the change rate (%) of the impedance as shown in FIG. 11. Therefore, it is possible to discriminate the sensor A and the sensor B by setting a predetermined discrimination criterion value DHR according to the change rate. Further, discrimination may be made using both of a difference between impedances and a change rate of the impedance when there are a humidity region in which it is easier to make the discrimination in the case of using the difference between impedances and a humidity region in which it is easier to make the discrimination in the case of using the change rate of the impedance by the humidity region depending on characteristics of the discriminated humidity sensor. For example, discrimination may be made using the difference between impedances in a low humidity region and discrimination may be made using the change rate of the impedance in a middle humidity region and a high humidity region (see FIGS. 6 and 11).

In the above-described exemplary embodiments, a high frequency (one example of a first frequency or a second frequency) of a PWM signal has been set at an upper limit value (100 kHz) capable of being switched by the CPU 25 and a low frequency (one example of a second frequency or a first frequency) has been set at a lower limit value (100 Hz) capable of being switched by the CPU 25. However, the invention is not limited thereto. The "first frequency" and the "second frequency" may be a frequency previously decided by experiment, etc., so as to obtain a difference between impedances or a change rate of the impedance for discriminating a humidity sensor by different frequencies in brief.

In addition to the above-described exemplary embodiments, it may be configured such that, when a difference between impedances and/or a change rate of the impedance is equal to or less than a predetermined value, the CPU 25 (a discriminating unit) judges that some abnormality occurs in the humidity detecting device 20 and generates a notification signal for providing notification of the abnormality. For example, as shown in FIG. 6, when a difference between impedances is equal to or less than a predetermined value DZth (for example, 2 kΩ), the CPU 25 generates a notification signal Si and supplies the notification signal Si to an external notification device (not shown). In addition, the notification device may be provided in the humidity detecting device 20.

In this case, in a resistance variable type humidity sensor, the impedance normally changes according to a frequency (driving frequency) of an applied voltage from the characteristics. Thus, abnormality probably occurs in the humidity sensor 23 or a peripheral circuit (for example, a circuit for switching a driving frequency) when a predetermined difference between impedances and/or a change rate of the impedance is not detected with respect to different driving frequencies. Therefore, abnormality in the humidity detecting device is detected based on the difference between impedances and/or the change rate of the impedance and a predetermined value and, for example, the notification signal is supplied to the external notification device and a user can be notified of the abnormality in the humidity detecting device by the notification device.

In the above-described exemplary embodiments, the example of discriminating the humidity sensor 23 based on a predetermined discrimination criterion has been shown. Alternatively, the humidity sensor 23 may be discriminated without being compared with the discrimination criterion when the humidity sensor 23 can be discriminated by a difference between impedances and/or a change rate of the impedance simply.

In the above-described exemplary embodiments, the example of changing a discrimination criterion according to ambient temperature and ambient humidity has been shown. Alternatively, the discrimination criterion may be changed according to ambient temperature or ambient humidity.

What is claimed is:

1. A humidity detecting device comprising:
    a humidity sensor that detects a humidity based on a change in an impedance, and that generates a humidity detection signal based on an applied alternating current (AC) voltage;
    an applying unit that applies the AC voltage to the humidity sensor;
    a detecting unit that detects a first impedance of the humidity sensor based on a first frequency of the AC voltage, and that detects a second impedance of the humidity sensor based on a second frequency of the AC voltage, wherein the first frequency and the second frequency are different;
    a switching unit that switches a frequency of the AC voltage to one of the first frequency and the second frequency;
    a temperature sensor that detects an ambient temperature of the humidity sensor;
    a processor; and
    memory operatively coupled to the processor and storing computer readable instructions that, when executed by the processor, cause the humidity detecting device to function as:
        a calculating unit that calculates one of a difference and a change rate between the detected first impedance and the detected second impedance;
        a discriminating unit that discriminates a kind of the humidity sensor based on the one of the difference and the change rate between the detected first impedance and the detected second impedance, wherein the humidity sensor corresponds to one of a plurality of kinds of humidity sensors; and
        a control unit that performs processing corresponding to the discriminated kind of the humidity sensor when the humidity detecting device detects the humidity.

2. The humidity detecting device according to claim 1, wherein a switchable upper limit frequency value corresponds to one of the first frequency and the second frequency, and
    wherein a switchable lower limit frequency value corresponds to another one of the first frequency and the second frequency.

3. The humidity detecting device according to claim 1, wherein the discriminating unit is further configured to discriminate the humidity sensor by comparing a predetermined discrimination criterion with the one of the difference and the change rate, and
    wherein the humidity detecting device further comprises memory storing computer readable instructions that, when executed by the processor, cause the humidity detecting device to function as:
        a changing unit that changes the discrimination criterion according to one of the detected ambient temperature and the detected humidity.

4. The humidity detecting device according to claim 1, wherein the applying unit comprises:
    a first applying part that applies the AC voltage to a first end of the humidity sensor;
    a second applying part, which comprises a first resistor connected to a second end of the humidity sensor and having a first resistance value, and that applies a voltage with a phase opposite to that of the AC voltage applied by the first applying part; and
    a third applying part, which comprises a second resistor connected to the second end of the humidity sensor and having a second resistance value different from the first resistance value, and that applies a voltage with a phase opposite to that of the AC voltage applied by the first applying part, and
    wherein the control unit selects one of the second applying part and the third applying part according to the discriminated humidity sensor.

5. The humidity detecting device according to claim 1, further comprising:
    a storage unit that stores a plurality of temperature correction tables corresponding to the discriminated humidity sensor, each of the plurality of temperature correction tables associating data of the humidity detection signal with detected humidity data according to the detected ambient temperature,
    wherein the control unit reads the detected humidity data corresponding to the humidity detection signal data out of the temperature correction table corresponding to the discriminated humidity sensor among the plurality of temperature correction tables.

6. The humidity detecting device according to claim 1, further comprising:
    a storage unit that stores a criterion temperature correction table for associating data of the humidity detection signal with detected humidity data according to the detected ambient temperature,
    wherein the control unit alters the detected humidity data read out of the criterion temperature correction table according to the discriminated humidity sensor.

7. The humidity detecting device according to claim 1, wherein, when the one of the difference and the change rate is equal to or less than a predetermined value, the discriminating unit judges that an abnormality is occurring in the humidity detecting device and generates a notification signal for providing a notification of the abnormality.

8. An image forming apparatus comprising:
    a humidity detecting device comprising:
        a humidity sensor that detects a humidity based on a change in an impedance, and that generates a humidity detection signal based on an applied alternating current (AC) voltage;
        an applying unit that applies the AC voltage to the humidity sensor;
        a detecting unit that detects a first impedance of the humidity sensor based on a first frequency of the AC voltage, and that detects a second impedance of the humidity sensor based on a second frequency of the AC voltage, wherein the first frequency and the second frequency are different;
        a switching unit that switches a frequency of the AC voltage to one of the first frequency and the second frequency;

a temperature sensor that detects an ambient temperature of the humidity sensor;
a processor; and
memory operatively coupled to the processor and storing computer readable instructions that, when executed by the processor, cause the humidity detecting device to function as:
  a calculating unit that calculates one of a difference and a change rate between the detected first impedance and the detected second impedance;
  a discriminating unit that discriminates a kind of the humidity sensor based on the one of the difference and the change rate between the detected first impedance and the detected second impedance, wherein the humidity sensor corresponds to one of a plurality of kinds of humidity sensors; and
  a control unit that performs processing corresponding to the discriminated kind of the humidity sensor when the humidity detecting device detects the humidity;
an image forming unit that forms an image on a sheet based on image data; and
an apparatus control unit that controls image forming processing of the image forming unit based on the humidity detected by the humidity detecting device.

9. The image forming apparatus according to claim 8, wherein a switchable upper limit frequency value corresponds to one of the first frequency and the second frequency, and
wherein a switchable lower limit frequency value corresponds to another one of the first frequency and the second frequency.

10. The image forming apparatus according to claim 8, wherein the discriminating unit is further configured to discriminate the humidity sensor by comparing a predetermined discrimination criterion with the one of the difference and the change rate, and
wherein the humidity detecting device further comprises memory storing computer readable instructions that, when executed by the processor, cause the humidity detecting device to function as:
  a changing unit that changes the discrimination criterion according to one of the detected ambient temperature and the detected humidity.

11. The image forming apparatus according to claim 8, wherein the applying unit comprises:
  a first applying part that applies the AC voltage to a first end of the humidity sensor;
  a second applying part, which comprises a first resistor connected to a second end of the humidity sensor and having a first resistance value, and that applies a voltage with a phase opposite to that of the AC voltage applied by the first applying part; and
  a third applying part, which comprises a second resistor connected to the second end of the humidity sensor and having a second resistance value different from the first resistance value, and that applies a voltage with a phase opposite to that of the AC voltage applied by the first applying part, and
wherein the control unit selects one of the second applying part and the third applying part according to the discriminated humidity sensor.

12. The image forming apparatus according to claim 8, wherein the humidity detecting device further comprises:
  a storage unit that stores a plurality of temperature correction tables corresponding to the discriminated humidity sensor, each of the plurality of temperature correction tables associating data of the humidity detection signal with detected humidity data according to the detected ambient temperature,
  wherein the control unit reads the detected humidity data corresponding to the humidity detection signal data out of the temperature correction table corresponding to the discriminated humidity sensor among the plurality of temperature correction tables.

13. The image forming apparatus according to claim 8, wherein the humidity detecting device further comprises:
  a storage unit that stores a criterion temperature correction table for associating data of the humidity detection signal with detected humidity data according to the detected ambient temperature,
  wherein the control unit alters the detected humidity data read out of the criterion temperature correction table according to the discriminated humidity sensor.

14. The image forming apparatus according to claim 8, wherein, when the one of the difference and the change rate is equal to or less than a predetermined value, the discriminating unit judges that an abnormality is occurring in the humidity detecting device and generates a notification signal for providing a notification of the abnormality.

* * * * *